(12) United States Patent
Dotta

(10) Patent No.: US 6,719,137 B2
(45) Date of Patent: Apr. 13, 2004

(54) SEALED PACKAGE FOR ADHESIVE WOUND DRESSING, AND APPARATUS THEREFORE

(76) Inventor: Angelo Dotta, Via Alamandini No. 10, 40136 Bologna (IT)

( * ) Notice: Subject to any disclaimer, the term of this patent is extended or adjusted under 35 U.S.C. 154(b) by 0 days.

(21) Appl. No.: 10/223,111

(22) Filed: Aug. 15, 2002

(65) Prior Publication Data

US 2002/0195367 A1 Dec. 26, 2002

Related U.S. Application Data

(63) Continuation of application No. PCT/EP00/01377, filed on Feb. 18, 2000.

(51) Int. Cl.$^7$ .......................... A61F 13/00; A61L 15/00
(52) U.S. Cl. .......................... 206/441; 206/440; 602/57
(58) Field of Search ............................ 206/440, 441; 602/41–43, 52, 54, 57, 58

(56) References Cited

U.S. PATENT DOCUMENTS

| 2,721,550 | A | * | 10/1955 | Banff .......................... 206/441 |
| 3,183,910 | A | | 5/1965 | Patterson |
| 3,245,855 | A | * | 4/1966 | Stenvall ....................... 602/57 |
| 3,797,495 | A | | 3/1974 | Schmidt |
| 4,235,337 | A | * | 11/1980 | Dotta .......................... 206/441 |
| 4,418,822 | A | * | 12/1983 | Dotta .......................... 206/441 |
| 4,656,674 | A | | 4/1987 | Medwell |
| 5,397,297 | A | * | 3/1995 | Hunter ......................... 602/57 |
| 5,628,724 | A | * | 5/1997 | DeBusk et al. ............... 206/440 |
| 5,628,741 | A | | 5/1997 | Buell et al. |
| 5,723,087 | A | | 3/1998 | Chappell et al. |
| 6,010,002 | A | * | 1/2000 | Petterson ..................... 206/441 |

FOREIGN PATENT DOCUMENTS

| EP | 0 579 030 | 1/1994 |
| EP | 0 810 078 | 12/1997 |
| EP | 0 848 937 | 6/1998 |
| GB | 2 273 279 | 6/1994 |
| WO | 97/23398 | 7/1997 |

* cited by examiner

*Primary Examiner*—Luan K. Bui
(74) *Attorney, Agent, or Firm*—Katten Muchin Zavis Rosenman

(57) ABSTRACT

The invention refers to a preferential rapidly opening package for adhesive bandages comprising a wrapping, obtained by the union of two half-wrappers ($I_1$, $I_2$), in which is enclosed the adhesive bandage provided with an adhesive support (A), and in which the pulling of the ends of said half-wrappers ($I_1$, $I_2$) causes the preferential removal of one of said half-wrappers ($I_1$, $I_2$).

5 Claims, 5 Drawing Sheets

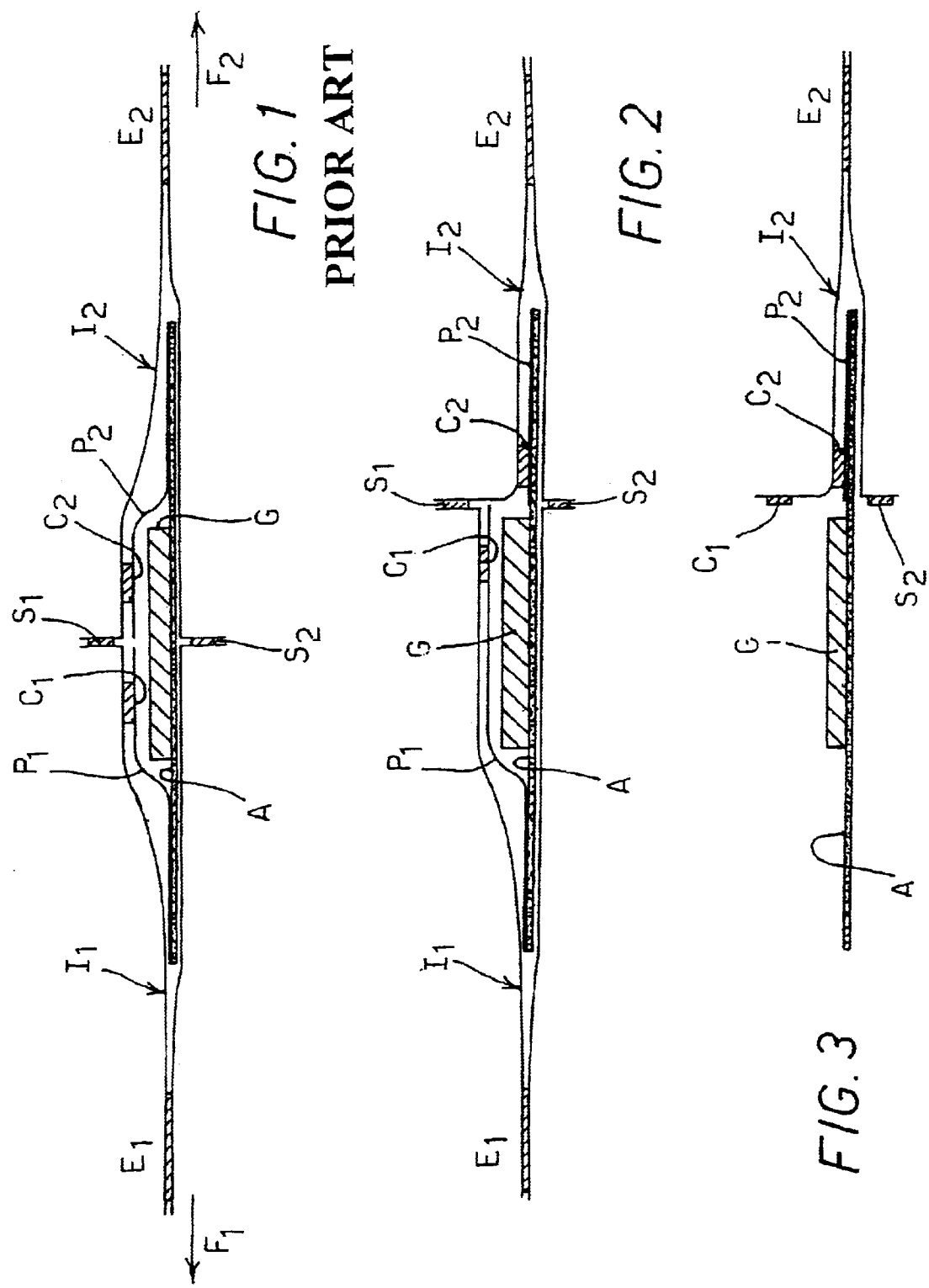

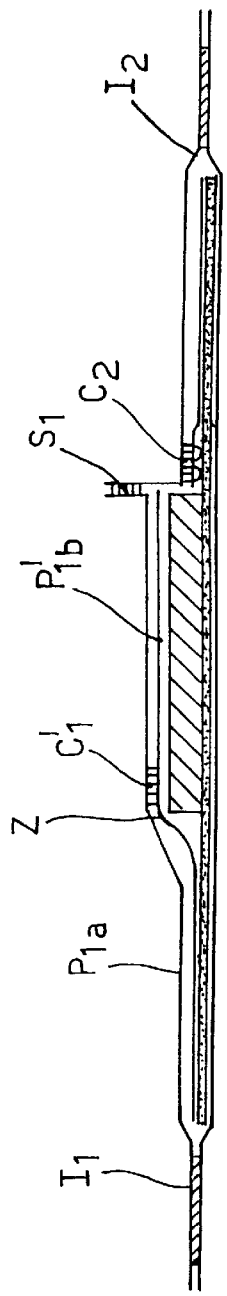
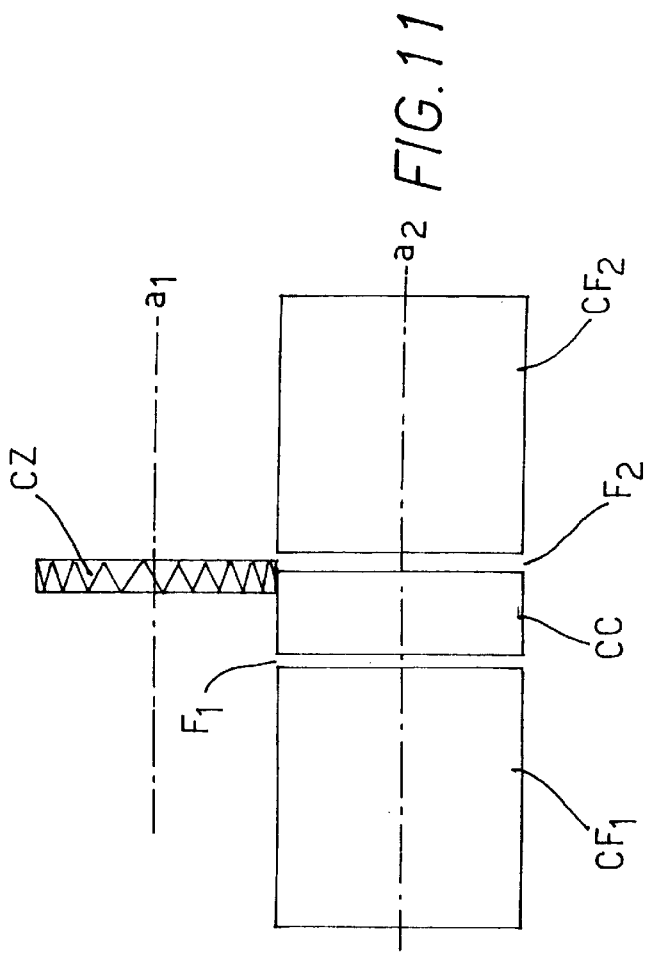

SEALED PACKAGE FOR ADHESIVE WOUND DRESSING, AND APPARATUS THEREFORE

This is a continuation of Applications No. PCT/EP00/01377, filed Feb. 18, 2000.

The present invention refers to a new sealed package for wound dressing adhesive tapes and bandages in general, which allows a preferential rapidly opening.

The invention moreover refers to the means for manufacturing that package.

The well known dressing adhesive tapes comprise an adhesive support housing a wound dressing pad or similar, covered by two protecting films which must be manually removed before the application.

Generally, said dressing adhesive tapes are packed into envelopes, coverings or wrappers, made by two paper or plastic sheets, which can be opened acting on two lateral flaps.

For a more practical and hygienic use of the dressing adhesive tapes, have been patented and manufactured rapidly opening packages which allow to open the package and to remove the protective films simply by pulling out the ends of the same covering, which breaks in two half-packages.

U.S. Pat. No. 3,245,855 discloses a bandage having a protective cover strip provided with a series of indentation so as to facilitate the removal thereof from the adhesive support.

The present invention is a substantial improvement of a package of the type disclosed in the Dotta patent U.S. Pat. No. 4,235,337.

The product disclosed in the above mentioned patent has an undifferentiated opening system. Indeed, pulling the ends of the package, the user will draw first the left or right half-package, indifferently, uncovering the corresponding part of the tape. The uncovering of the bandage will then be completed by drawing, again by pulling, the remaining portion of the package. In this solution it is necessary that the two bandage parts to be uncovered are equal, each corresponding to a half part of the bandage, in order to avoid the risk, in case the two parts are differently dimensioned, that a smaller portion is uncovered firstly, instead of the larger one.

When the bandage is used, it is however a problem for the user to correctly position the bandage relatively to the wound part, because only half bandage is visible and available. The user is led to entirely uncover the bandage—before its application—keeping between two fingers the uncovered adhesive part and drawing out the remaining half-package.

In order to avoid this improper use, which could make void the practicality and sterility of the product, it should be better that the user had available, after the removal of the first half-package, an uncovered bandage portion leaving open the whole dressing pad, so that it is easier to position the bandage grasping the remaining half-package and drawing it away only when the part of the bandage comprising the dressing pad has been applied to the skin.

Main object of the present invention is therefore to meet this need providing a predetermined preferential opening in the package. Advantageously, according to the invention, about ⅔ of the adhesive bandage will result always uncovered after the first drawing of the package; this can be accomplished maintaining the possibility of manufacturing the package according to the method disclosed in the Dotta patent U.S. Pat. No. 4,418,822 which allows to reuse the protective sheet or liner of the adhesive support for obtaining the protective films of the bandage.

The characteristics and advantages of the present invention will result clearly from the following description of a preferred embodiment, presented as a non-limitative example, and with reference to the attached drawings, in which:

FIG. 1 shows schematically a rapidly opening package for adhesive bandages according to the prior art;

FIG. 2 shows schematically an asymmetrical package for adhesive bandages according to the present invention;

FIG. 3 shows the package of FIG. 2, partially opened;

FIG. 10 is longitudinal sectional view of the package of FIG. 9; and

FIG. 11 is a schematic view of the device for realising the zig-zag cut.

As shown in FIG. 1, the package for adhesive bandages according to the prior art is obtained by means of a paper wrapping made of two half-wrappers $I_1$ and $I_2$, welded together in correspondence of the areas $S_1$, $S_2$, $E_1$ and $E_2$.

Inside the package shown in FIG. 1 is housed an adhesive bandage consisting of a dressing pad G fixed to a strip of adhesive support A having a substantially rectangular shape and having an adhesive surface.

Between the half-wrappers $I_1$ and $I_2$ and the adhesive bandage are moreover provided two protective films $P_1$ and $P_2$, generally made of silicone paper, attached to the corresponding half-wrappers $I_1$ and $I_2$ of the paper wrapping by means of a bonding agent in correspondence of the areas $C_1$ and $C_2$.

According to the example of FIG. 1, when two pulling forces are applied in opposite directions to the ends $E_1$ and $E_2$ of the package, according to the arrows $F_1$ and $F_2$, the half-wrapper $I_1$ or the half-wrapper $I_2$, indifferently, and the corresponding film $P_1$ or $P_2$, will be initially detached, due to the symmetry of the components.

A first step towards the solution of the problem of how differentiating the opening of the package 11, 12 is given by providing an asymmetrical package and protective films having different dimensions. In particular, as shown in FIG. 2, the film $P_1$ will extend to cover all the dressing pad G, while the film $P_2$ will be reduced to the dimensions of the adhesive support below.

According to this configuration, pulling out the ends $E_1$ and $E_2$ of the package, the whole dressing pad G, and the portion of the adhesive support A on the same side (on the left in FIG. 2), will be uncovered firstly.

This happens because the film $P_1$ has its initial portion in contact with the dressing pad G and therefore is completely or in part separated from the adhesive present on the adhesive layer A which, on the contrary, holds in place the film $P_2$.

At the end of this phase, FIG. 3, about ⅔ of the adhesive bandage are therefore free from the wrapping, as the half-wrapper $I_1$ has been completely removed.

At this point, the user applies the uncovered portion of the adhesive support A on the skin and, pulling the opposite end $E_2$ of the half-wrapper $I_2$, will uncover the remaining part of the adhesive support.

However, that operation could be difficult because the half-wrapper $I_2$, which is still in place, must be pulled according to a direction substantially parallel to the adherence plane of the film $P_2$ to the adhesive support below. Said attempt will generally cause a permanent distortion or a rupture in the adhesive support of the bandage.

The problem to be solved will be therefore how to obtain the separation of the protective film $P_2$ once the film $P_1$ has been removed and the adhesive bandage has been applied to the wound.

Figure 4:
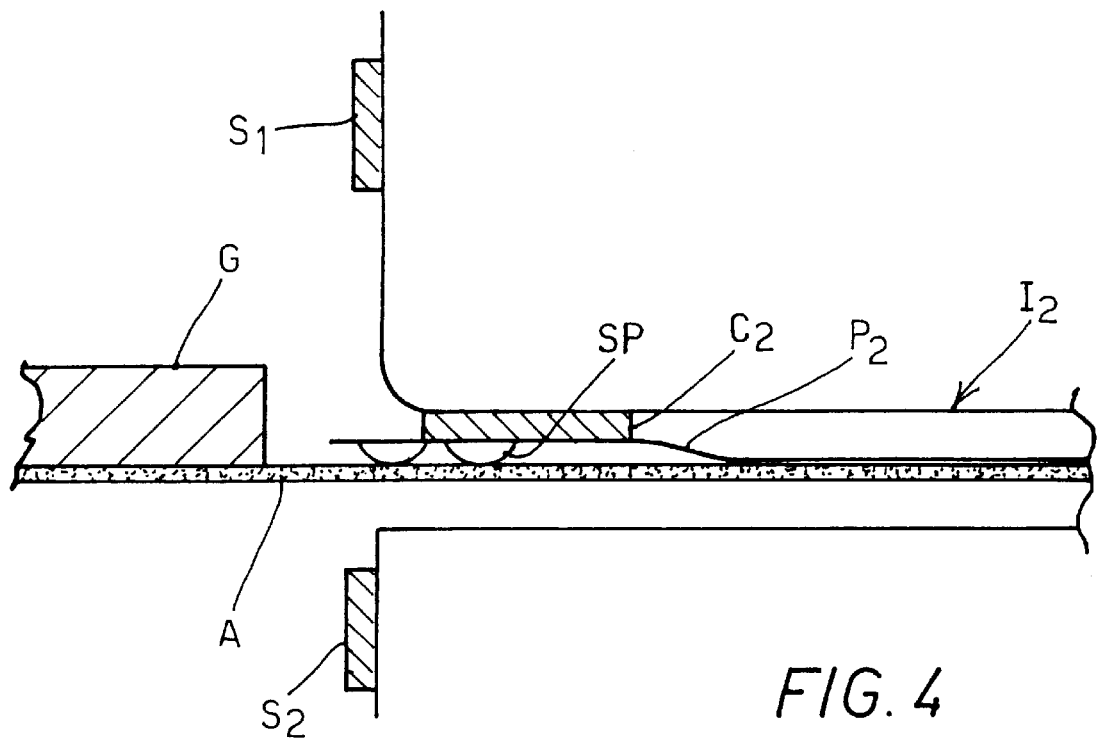
FIG. 4 is partial enlarged sectional view of the package according to the invention, partially opened.

In FIG. 4 it is shown schematically the solution idea of the above mentioned further problem, wherein the protective film $P_2$ is provided with, in correspondence of the area glued to the half-wrapper $I_2$, an alteration or distortion for reducing the surface in contact with the adhesive, i.e. an embossing causing a plurality of projections SP.

Figure 5:
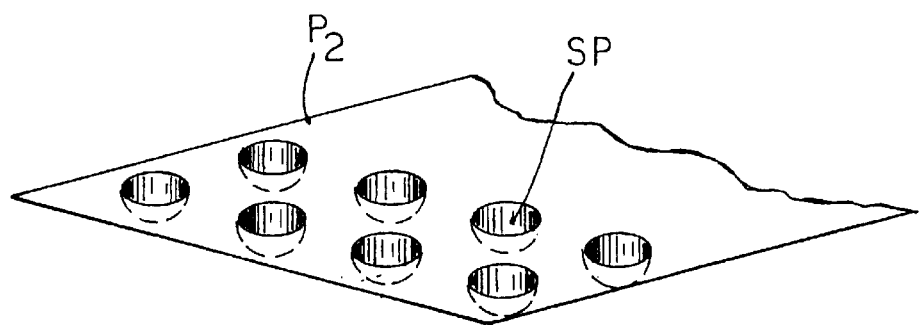
FIG. 5 is an enlarged view of a portion of a protective film realised according to the invention.

As clearly shown in FIG. 5 the projections SP have preferably the shape of an hemisphere (with a diameter of about 2 mm) and are arranged on two or more staggered lines, as a honeycomb structure.

According to that configuration, the surface of the film $P_2$ actually in contact with the adhesive of the support A is largely reduced, and consequently it is reduced the resistance to removal.

Moreover, the higher thickness of the protective film $P_2$ in correspondence of the projections SP (about 1 mm instead of 0.07 mm), relatively to the reduced area of the anchoring area $C_2$, causes a torsion effect on the film $P_2$ which contributes to facilitate the separation of the film itself from the adhesive support A.

In this way, the film $P_2$ can be removed with a relatively lower pulling force, so that the adhesive bandage is not deformed, said force being however greater then the force needed for opening the package and uncovering the ⅔ of the bandage, due to the low adherence to the adhesive of the film P1.

Obviously, the idea underlying the present invention can be accomplished by means of another pressing method, other than embossing, which reduces the contact surface of the protective layer to be removed, which is in contact with the adhesive. In order to obtain the same effect it will be possible to perform, for instance, a knurl, a perforation with the removal or not of the relative cutting, an indentation, etc. This means that the pressing operation could produce concavities, instead of convexities, facing the adhesive, as well as simply cut out areas; the essential thing is that the contact surface is reduced and, preferably, that the film thickness is increased.

Figure 6:
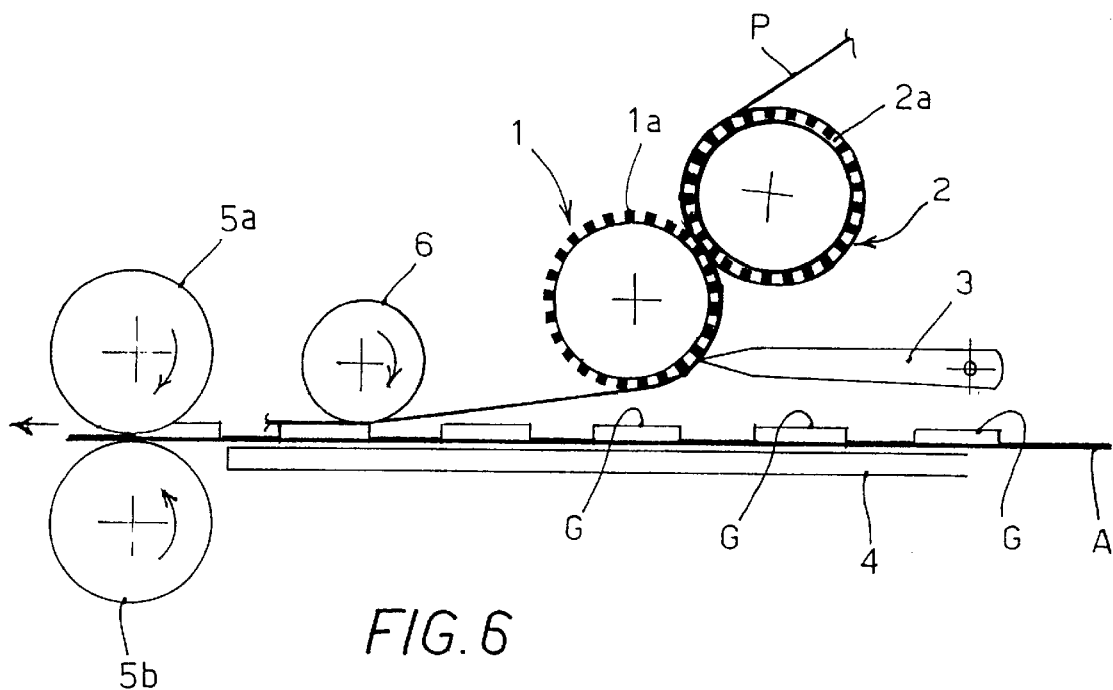
FIG. 6 is a schematic view of an apparatus for the manufacturing of the package according to the invention.
Figure 7:
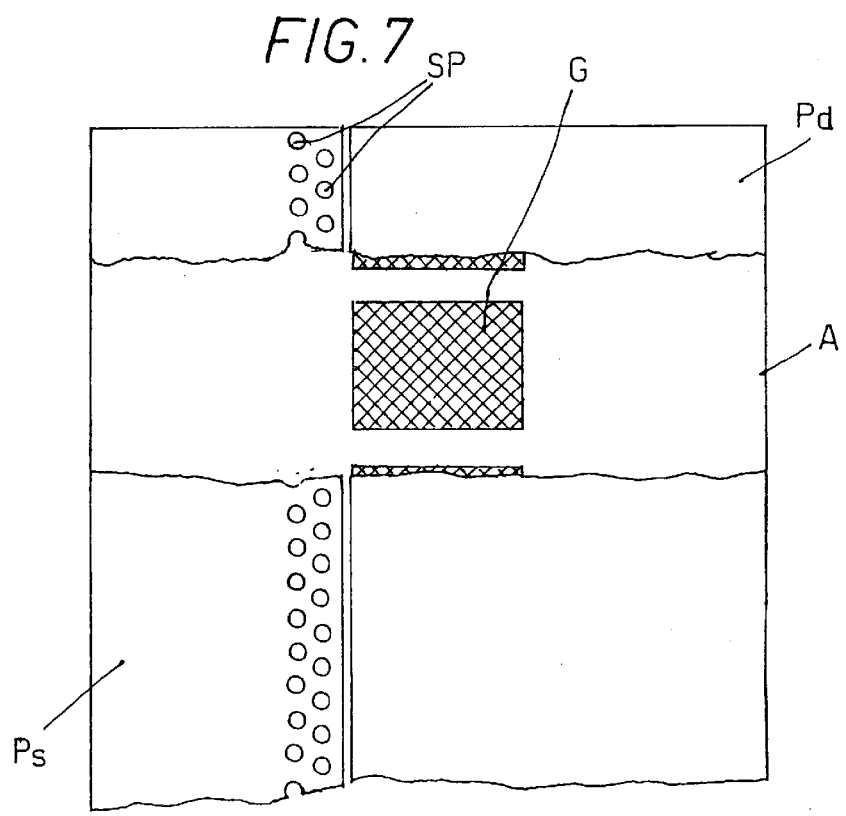
FIG. 7 is a schematic partial top view of a manufacturing phase of the package according to the invention.

With reference to FIGS. 6 and 7 it is shown schematically an apparatus for producing the protective film according to the invention.

Said apparatus comprises substantially a couple of rotating dies male 1 and female 2, through which passes the protective film P, preferably obtained reusing the protective sheet previously removed from the adhesive support A.

Said film P is generally made of silicone paper and is separated, by means of a longitudinal cut, in the two parallel tapes $P_S$ and $P_D$ which will be applied on the adhesive bandages passing on the feeding plane 4.

The rotating dies 1 and 2 are obtained by means of metallic cylinders on which are obtained, respectively, a plurality of hemispheric projections or punches 1a and a plurality of complementary recesses 2a in order to produce a plurality of projections SP on the film $P_S$.

Said dies will be opportunely heated if the protective materials used are thermoplastic materials instead of silicone paper or similar.

A knife 3 is moreover provided for cutting the protective material P in a longitudinal direction in order to obtain the left $P_S$ and the right $P_D$ films, which will be applied on the adhesive bandage.

In order to allow the cut of the film P by means of the knife 3, a corresponding circumferential groove is provided on the male die 1 laterally to the projections or punches 1a.

Obviously, alternatively to the knife 3, can be provided a circular knife.

Downstream the rotating dies 1 and 2 is provided a roller 6 which presses the protective film P on the adhesive support A, to which the dressing pads G have been previously fixed according to well known techniques.

A couple of coupling and feeding rollers 5a and 5b is moreover provided for feeding the protective films $P_S$ and $P_D$ and the adhesive support A before next working phases, that will be performed according to prior art techniques.

Advantageously, according to the invention, the punches or projections 1a are arranged staggered according to a honeycomb pattern, so that, during rotation of the dies 1 and 2, one punch 1a is always coupled to a corresponding cavity 2a.

Consequently, it is not needed that the rotating dies 1 and 2 are motor-driven and/or synchronised by means of gears, this function being accomplished by the co-operation between punches 1a and cavities 2a during the passage of the protective film P.

Naturally the package disclosed may also be realised with two or more protective films which can be obtained, for instance, by cutting by means of a cutting device similar to that disclosed.

Referring again to FIG. 2, it can be noted that the film $P_1$ has a portion relatively large which is over the dressing pad G and that therefore is not welded to the wrapper $I_1$, nor engaged with the adhesive support A.

In order to be correctly removed, the film $P_1$ should fold itself describing a "S", as happens in the packages realised according to the teachings of the Dotta patent U.S. Pat. No. 4,235,337.

Figure 8:
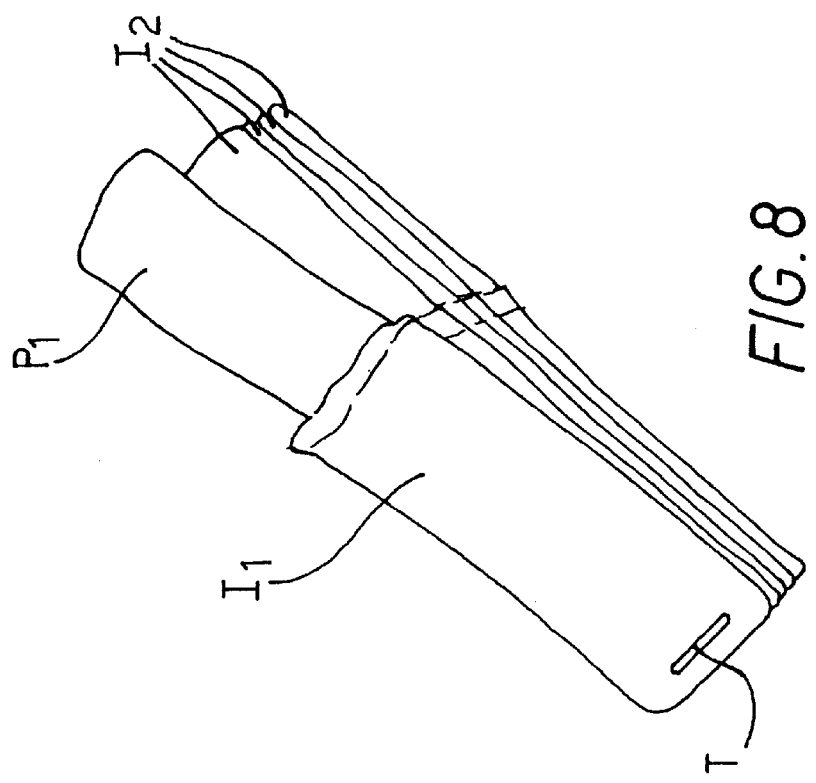
FIG. 8 shows a plurality of bandage packages arranged as bellows.

Moreover, it is to be noted that the film $P_1$, due to its overall length, considerably projects from the half-wrapper $I_1$, when the wrapping has been opened, causing an obstacle which is undesirable and causes particularly troublesome consequences when more adhesive bandages are packaged as bellows as shown in FIG. 8, because the residual film could cover next package.

Figure 9:
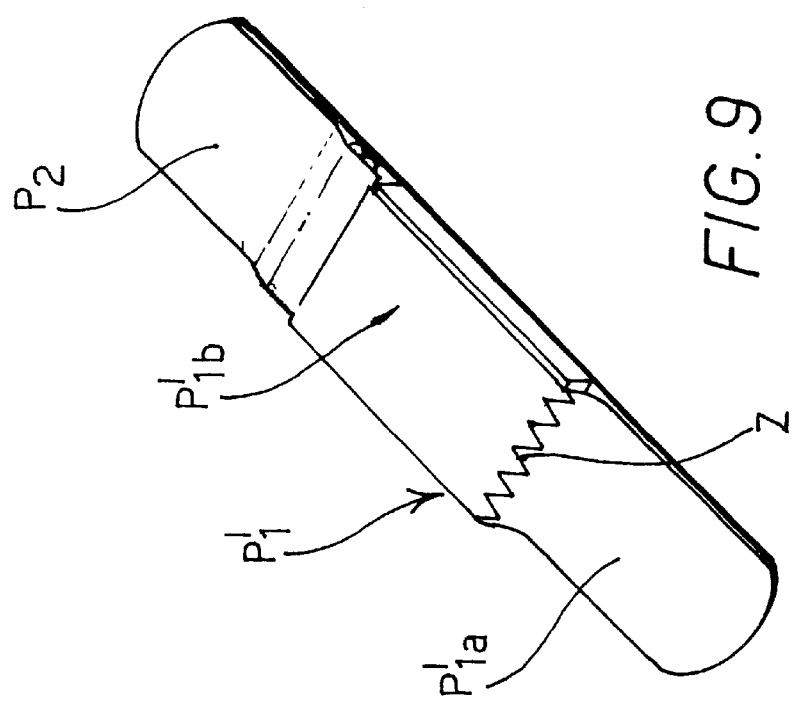
FIG. 9 is a perspective view of another embodiment of the invention.

According to an alternative embodiment of the present invention, shown in FIGS. 9 and 10, it is provided that the gluing point $C_1'$ is placed near the outer edge of the dressing pad G (on the left in FIGS. 10 and 11) and that on the film $P_1'$, in correspondence of the outer edge of the dressing pad G, is provided a transversal incision which allows the "S" bending of the film itself.

With reference to FIG. 9 it is shown, in a perspective view, the adhesive bandage packaged according to this embodiment of the invention wherein the film $P_1'$ comprises a portion $P_1'_a$, completely engaged with the adhesive, and a portion $P_1'_b$ which is raised relative to the portion $P_1'_a$, being superimposed to the dressing pad G. In the area separating the two portions $P_1'_a$ and $P_1'_b$ is provided a zig-zag incision Z which facilitates folding of the portion $P_1'_b$ on the portion $P_1'_a$.

Referring now to FIG. 10 it is evident that, exercising a suitable pulling force for opening the package, the film $P_1'$ tends to fold over itself in correspondence of the incision Z, being the incision Z comprised between the glue $C_1'$ and the adhesive support A.

Again with reference to FIG. 10, it is as much evident that, when the half-wrapper $I_1'$ has been removed, the portion of the film $P_{1\,a}'$ folded onto the portion $P_{1\,b}'$ will project little from the edge of the half-wrapper $I_1'$, having the two film portions substantially the same length.

In FIG. 11 it is shown part of the apparatus for carrying out the incision Z.

As it is shown in FIG. 11, the incision Z on the film $P_1'$ is obtained by a circular knife CZ rotating around the axis $a_1$ in co-operation with the counter cylinder CC to which are placed side by side the cylinders $CF_1$ and $CF_2$, both rotating around axis $a_2$.

In FIG. 11 it is shown, with the reference $F_1$, a slit provided between the cylinders CC and $CF_1$, and with the reference $F_2$, a slit provided between the cylinders CC and $CF_2$. The slit $F_2$, provides an empty area which can be increased or reduced moving the cylinder CC on the left or on the right along the rotation axis $a_2$ using the slit $F_1$ for varying the counter surface between cylinders CZ and CC.

In order to realise the zig-zag cut, the protective material to be cut is moved on the cylinder $CF_1$, CC and $CF_2$ under the knife CZ (opportunely pressed against the cylinder CC). The positioning of the cylinder CC between Cylinders $CF_1$ and $CF_2$ determines the width of the incision Z and, consequently, the more or less weakening of the protective film.

It is to be noted that the position of the gluing point $C_1'$ and the position of the incision Z have been presented as a non limitative example, and are to be considered comprised in the same invention solutions in which the area Z and the gluing $C_1'$ are positioned differently.

What is claimed is:

1. Preferential rapidly opening package for adhesive bandages in which are provided:

an adhesive bandage, comprising an adhesive support (A) having a bandage compress or pad (G), provided with protective material films ($P_1$, $P_2$) which can be separated from said adhesive support before the application of said adhesive bandage;

a wrapping ($I_1$, $I_2$) enclosing said adhesive bandage, which can be separated, by pulling its ends ($E_1$, $E_2$), in two half-wrappers anchored to corresponding protective material films ($P_1$, $P_2$) and having different dimensions as a function of the dimensions of the films ($P_1$, $P_2$) to which they are anchored, characterised in that a first one of said films ($P_1$, $P_2$) extends on one side up to cover substantially the whole bandage pad (G) and a second one of said films extends on the other side up to cover substantially only the remaining adhesive, whereby when said ends ($E_1$, $E_2$) are pulled out the isolation from the adhesive support due to the bandage pad (G) causes said first film ($P_1$, $P_2$) to be uncovered firstly with respect to said second film ($P_1$, $P_2$) and in that the surface of said second film ($P_1$, $P_2$) in contact with said adhesive support (A) is provided with a plurality of projections and/or recesses in correspondence of the anchoring area of said second film ($P_1$, $P_2$) to its half-wrapper thus reducing the contact surface with said adhesive support (A) so as to facilitate the removal of said second film once the first film has been removed and the adhesive support is applied on the skin.

2. Package according to claim 1, characterised in that said first protective material film (P1, P2) extending up to cover substantially the whole bandage pad (G), has in correspondence of or in proximity of the edge of the pad, a transversal weakening (Z) suitable for facilitating the folding of said film and has likewise a gluing/welding (C1') to the corresponding half-wrapper (I1, I2) in a middle position relatively to the pad (G) or near the weakening (Z).

3. Package according to claim 1, characterized in that said first and second films ($P_1$, $P_2$) are obtained from the protective sheet removed from an adhesive support recovered during manufacturing of the adhesive bandage.

4. Package according to the claim 1, characterised in that said projections and/or recesses are arranged in one or more transversal lines coupled and staggered, as a honeycomb structure, defining substantially an embossing of the protective material.

5. Package according to the claim 2, characterised in that the transversal weakening (Z) of the protective material consists of a zig-zag incision.

* * * * *